US00PP16747P3

(12) United States Plant Patent
Khanuja et al.

(10) Patent No.: US PP16,747 P3
(45) Date of Patent: Jul. 4, 2006

(54) **MINT PLANT *MENTHA SPICATA* L. VAR. *VIRIDIS* CHRISTENED AS 'GANGA'**

(50) Latin Name: *Mentha spicata L. var. viridis*
Varietal Denomination: Ganga

(75) Inventors: Suman P. S. Khanuja, New Delhi (IN); Sushil Kumar, New Delhi (IN); Ajit K. Shasany, New Delhi (IN); Sunita Dhawan, New Delhi (IN); Mahendra P. Darokar, New Delhi (IN); Arun K. Tripathy, New Delhi (IN); Sarita Satapathy, New Delhi (IN); Tiruppadiripuliyur R. S. Kumar, New Delhi (IN); Vivek K. Gupta, New Delhi (IN); Arvind K. Tripathi, New Delhi (IN); Soumya Awasthi, New Delhi (IN); Veena Prajapati, New Delhi (IN); Ali A. Naqvi, New Delhi (IN); Krishna K. Agrawal, New Delhi (IN); Janak R. Bahl, New Delhi (IN); Anil K. Singh, New Delhi (IN); Ateeque Ahmed, New Delhi (IN); Ravi P. Bansal, New Delhi (IN); Alok Krishna, New Delhi (IN); Dharmendra Saikia, New Delhi (IN)

(73) Assignees: Council of Scientific and Industrial Research, New Delhi (IN); Department of Biotechnology, New Delhi (IN)

( * ) Notice: Subject to any disclaimer, the term of this patent is extended or adjusted under 35 U.S.C. 154(b) by 0 days.

(21) Appl. No.: 10/840,289

(22) Filed: May 7, 2004

(65) Prior Publication Data

US 2005/0044600 P1 Feb. 24, 2005

Related U.S. Application Data

(63) Continuation-in-part of application No. 09/633,066, filed on Aug. 4, 2000, now abandoned.

(51) Int. Cl.
*A01H 5/00* (2006.01)

(52) U.S. Cl. ..... Plt./259

(58) Field of Classification Search ..... Plt./259
See application file for complete search history.

*Primary Examiner*—Anne Marie Grunberg
*Assistant Examiner*—June Hwu
(74) *Attorney, Agent, or Firm*—Ann S. Hobbs; Venable LLP

(57) ABSTRACT

The present invention relates to the development of a novel multiutility vigorously growing robust mint plant 'Ganga' of *Mentha spicata* L. var. *viridis* producing essential oil exhibiting anti-insect and anti-microbial activities and useful for agrochemical and pharmaceutical purposes.

3 Drawing Sheets

Figure 1A:
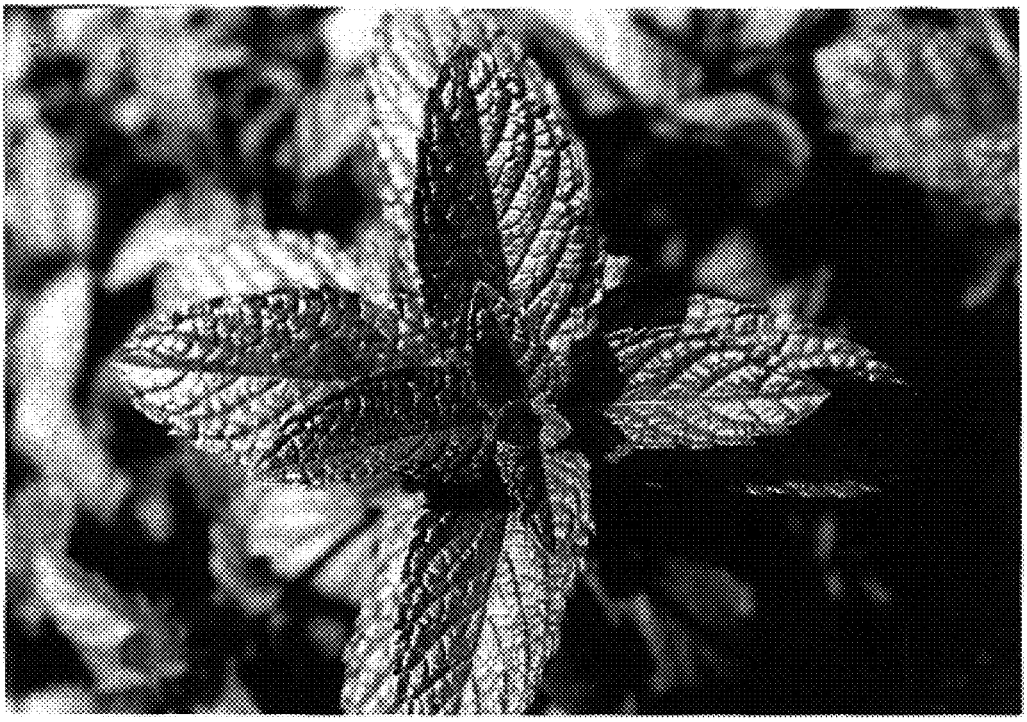

Latin name of the genus and species of the plant claimed: *Mentha spicata* L. var. *viridis*.
Variety denomination: 'Ganga'.

FIELD OF INVENTION

The present invention relates to a novel mint plant *Mentha spicata* L. var. *viridis* christened as 'Ganga'. Particularly, the invention relates to a novel mint plant, said plant being a somaclonal variant among in vitro raised large population of an accession of *Mentha spicata* L. var. *viridis* collected from the bank of the river Ganga.

BACKGROUND OF THE INVENTION

Consequent to the necessity felt for the pressing need of environmentally safe phytochemicals which can be of use as agro-protectants and bio-preservatives being non-toxic to human health the applicants resorted to short listing the available medicinal and aromatic plants. After much discussion and debate on practical feasibility, the genus *Mentha* was chosen for being the source of numerous bioactive monoterpenes of industrial importance and some taxa having traditional culinary use for human consumption. The main emphasis of the study was not to discover the novel compounds or chemicals but to develop and make available a plant naturally yielding chemicals in desired combination to exhibit the biological activities of utility to fit into the prevalent cropping systems for commercial purposes.

Mints are cultivated as industrial crops in several countries for the essential oil and contain high value monoterpenes, which find diverse uses in the cosmetic, pharmaceutical, food, confectionery and liquor industries. *Mentha spicata* L., commonly referred to as 'Spearmint' is the predominant source of flavour in various confectionery and food items due to the presence of carvone as the major component in its essential oil. The spearmint oil and its main constituent carvone are used extensively for various preparations ranging from medicine to flavored chewing gums, toothpastes and food products. The commercially important *Mentha spicata* L. predominantly has carvone in the essential oil but a taxonomically distinct variety, *viridis* of this species, has essential oil containing lower carvone content and some other components like limonene, piperitenone etc. In India this variety is cultivated widely in kitchen gardens for culinary use.

OBJECTS OF INVENTION

The main object of the invention is to develop an industrially useful plant in edible mint *M. spicata* var. *viridis* which is easy to cultivate and is non-toxic and safe for humans, plants, animals and environment.

Another object of the invention is to develop a plant with high yield of essential oil which could be used for controlling stored grain pests, inhibiting potato tuber sprouting and as antimicrobial agents to provide agroprotectants and antimicrobial formulations.

Another object of the present invention is to identify an use of the essential oil obtained from the novel variety 'Ganga' as herbal fumigant against stored grain pests selected from *Tribolium castaneum, Callosobruchus maculates, Rhyzopertha dominica* and *Sitophilus oryzae.*

Still another object of the present invention is to identify an use of the essential oil obtained from the novel variety 'Ganga' as anti-bacterial agent against bacteria selected from *Escherichia coli, Klebsiella pneumoniae, Streptococcus mutans, Staphylococcus epidermidis, Enterobacter aerogenes, Enterococcus feacalis* and *Staphylococcus aureus.*

Yet another object of the present invention is to use the essential oil obtained from the novel variety 'Ganga' as anti-fungal agent against dermatophytic and other fungi selected from *Aspergillus flavus, Aspergillus niger, Candida albicans, Microsporum gypseum* and *Sporothrix schenckii.*

Still another object was to establish the stability of plant genotype, multiply into uniform population for further propagation and provide the process of agronomically efficient method for growing the plants with least interference to the food crops.

Yet another object of the invention was to develop an industrially useful genotype of edibile mint, capable of being used as agroprotectant and biopreservent.

SUMMARY

The present invention provides a novel and distinctive variety of *Mentha spicata* L. var. *viridis* christened as 'Ganga'. This novel mint plant was asexually propagated vegetatively by suckers at the Institute of CIMAP, Lucknow, Uttar Pradesh, India. The novel mint plant suckers are produced in remarkably high quantities and is genetically stable for commercial cultivation. The plant exhibits unique profuse canopy and height surpassing all existing varieties. The essential oil of the novel mint plant grown for more than 60 days and later 45 days after each harvest shows extraordinary insecticidal properties against stored grain pests and hence has huge commercial potential in post harvest technology. In addition, the oil obtained from this plant exhibits anti-microbial and potato sprouting inhibition properties. Being an edible mint the use of its oil for insect control in stored grain and protecting the bulk produce like potato tubers is biosafe and environmentally compatible. Antimicrobial activities supports its use in pharmaceutical formulation as well as in food preservation.

DETAILED DESCRIPTION OF THE INVENTION

Thus, the invention provides a novel and distinct variety of *Mentha spicata* L. var. *viridis* christened as 'Ganga' and comprising the following combination of characters:

(a) exhibiting profuse globular canopy with rapid vegetative growth and attaining a height of about 68 to 77 cm in about 90 days, (b) having aerial mass of at least 275 g, and sucker mass of at least 340 g., (c) producing about 22 to 32 leaves per branch with an average leaf area of at least 8 $cm^2$, (d) having an average spread of less than 70 cm, (e) having distinct molecular profile by random amplified polymorphic DNA (RAPD) using 18 random primers distinguishing the plant from the other existing variety, (f) having characteristic light greenish leaves borne on purplish stem, (g) producing 0.35 to 0.65% oil, (h) being useful for food flavouring, ketchup/chutney, tea formulation and for flavouring beverages, and (i) producing essential oil containing a combination of 1.50 to 6.52% Limonene, 0.107 to 4.42% Carvone and 28.50 to 80.45% Piperitenone oxide, which can also be constituted artificially by combining these three components from any source in said ratios to yield multi-use formulation for agro-protectants biopreservants, antimicrobials, shelf life enhancer for agro-products and agricultural products.

In an embodiment, the plant 'Ganga' produces oil comprising a combination of:

i. 1.50 to 6.52% limonene, ii. 0.107 to 4.42% carvone and iii. 28.50 to 80.45% piperitenone.

In another embodiment, the oil from the plant 'Ganga' can be used as herbal fumigant against stored grain pests selected from *Tribolium castaneum, Callosobruchus maculates, Rhyzopertha dominica* and *Sitophilus oryzae.*

In yet another embodiment, the oil from the plant 'Ganga' can be used as anti-bacterial agent against bacteria selected from *Escherichia coli, Klebsiella pneumoniae, Streptococcus mutans, Staphylococcus epidermidis, Enterobacter aerogenes, Enterococcus feacalis* and *Staphylococcus aureus.*

In still another embodiment, the oil from the plant 'Ganga' can be used as anti-fungal agent against dermatophytic and other fungi selected from *Aspergillus flavus, Aspergillus niger, Candida albicans, Microsporum gypseum* and *Sporothrix schenckii.*

In another embodiment, the oil from the plant 'Ganga' can be used for preparation of formulation for antimicrobial products like mouth wash, surface disinfectants, hand disinfectants, shampoos, soaps, and like thereof and potato tuber sprouting inhibitors for storage of potato with enhanced shelf life and prevention of infecting microbes, biopreservant for raw, processed and cooked food commodities.

BRIEF DESCRIPTION OF THE ACCOMPANYING DRAWINGS

FIG. 1*a* shows top view of the plant shoot.

Figure 1B:
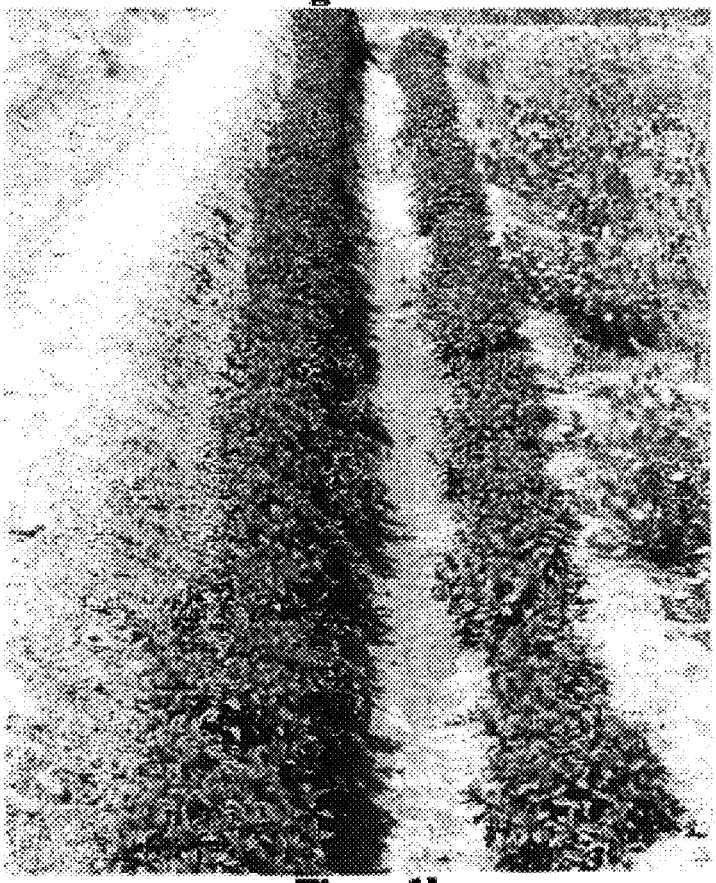

FIG. 1*b* shows Ganga growing in the slopes.

Figure 1C:
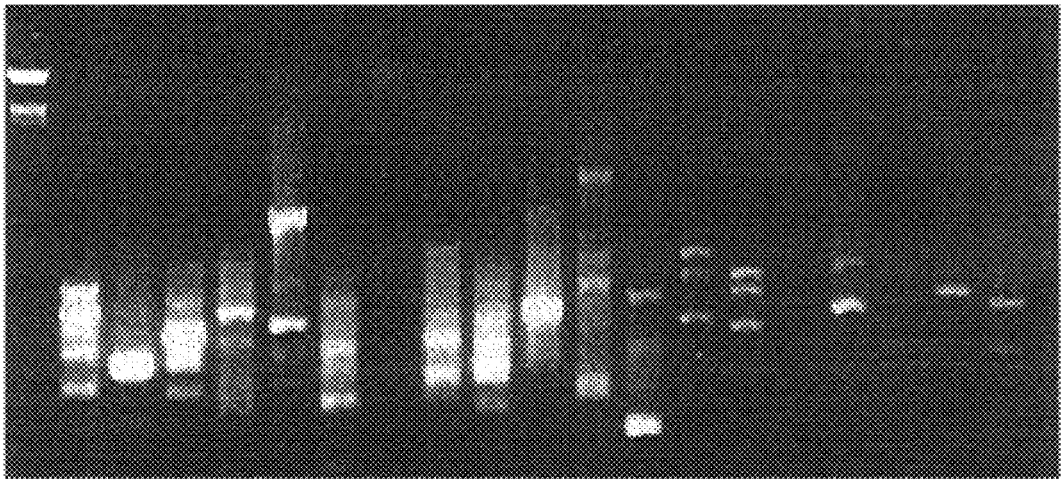

FIG. 1*c* shows unique RAPD profile of the plant 'Ganga'.

In FIG. 1*c:*

Lane 1: λ Hind III marker

Lanes 2–7: Profiles with primer AAATCGGAGC, GTCCTACTCG, GTCCTTAGCG, TGCGCGATCG, AACGTACGCG, GCACGCCGGA.

Lane 8: Blank

Lane 9–20: Profiles with primer CTATCGCCGC, CGGGATCCGC, GCGAATTCCG, CCCTGCAGGC, CCAAGCTTGC, GTGCAATGAG, AGGATACGTA, AAGATAGCGG, GGATCTGAAC, TTGTCTCAGG, CATCCCGAAC, GGACTCCACG.

Figure 1D:
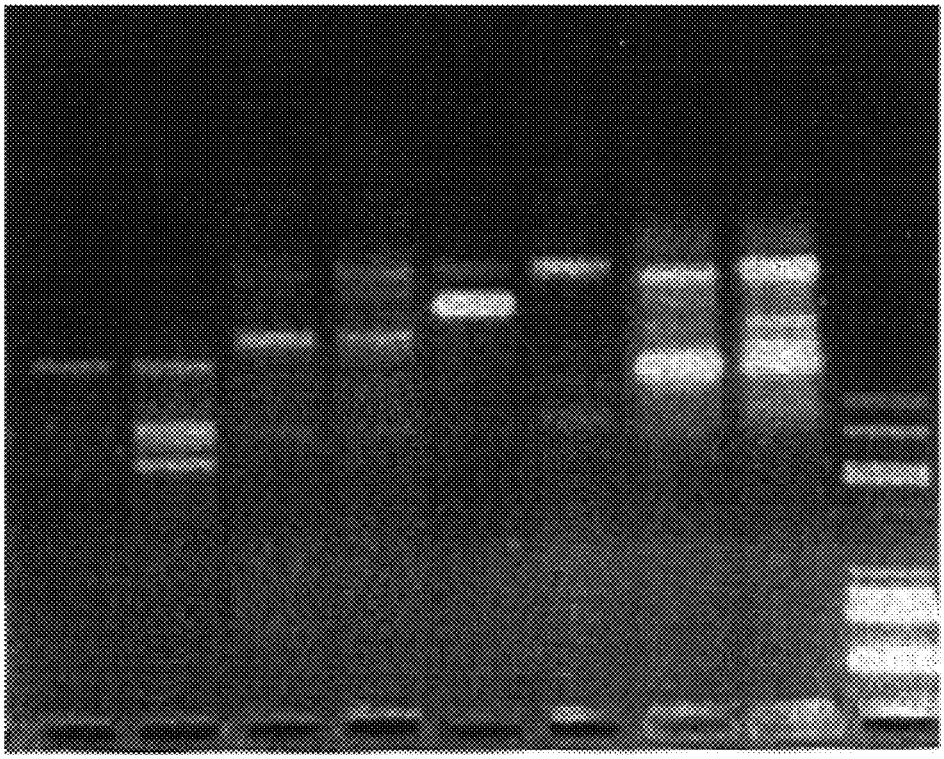

FIG. 1*d* shows comparison with Supriya.

In FIG. 1*d:*

Lane 1: λ Hind III+EcoRI marker

Lane 2, 3: Profile of Supriya and Ganga with primer AAATCGGAGC

Lane 4, 5: Profile of Supriya and Ganga with primer GTCCTACTCG

Lane 6, 7: Profile of Supriya and Ganga with primer CCAAGCTTGC

Lane 8, 9: Profile of Supriya and Ganga with primer CATCCCGAAC

The present invention is related to the development of a novel multiutility vigorously growing robust mint plant 'Ganga' of *Mentha spicata* L. var. *viridis*. This plant is unique and clearly distinct from all other existing varities of *Mentha spicata* L. var. *viridis*. This plant of *Mentha spicata L.* var. *viridis* is a novel in vitro selection from tissue culture raised population of molecular variants of an accession collected from the bank of the river Ganges and hence named 'Ganga'. The plant of invention grows equally well in plain, low and sloppy lands, can be maintained green throughout the year and shoot mass can be harvested with variable scheduling depending upon the requirement. The freshly harvested leaves upto one month after each harvest can be used for routine culinary purposes but interestingly the essential oil extracted from the old plants grown for 45 days or more exhibits anti-insect and anti-microbial activities and hence can be used for agrochemical and pharmaceutical purposes. This plant as such being of culinary use, offers biocompatible and safe source of agro-protectant of wider use.

The applicants collected one such naturally growing plant of *Mentha spicata* L var. *viridis* from the shore of the river Ganga and multiplied in a glass house to obtain an uniform population. In comparative bioassays of the *viridis* germplasm, the essential oil harvested from these plants showed high antifungal property and activity against stored grain insects. However the yield of the oil was 0.1 to 0.2%. Thus for inducing variability to select improved genotype (s), internodal explants were used to raise a population of calliclones for selection of somaclonal variants through detection of molecular polymorphism as described for *Mentha arvensis* (S. P. S. Khanuja, A. K. Shasany, S. Dhawan, S. Kumar, Rapid procedure for isolating somaclones of altered genotypes of *Mentha arvensis*. J. Med. Aroma. Plant Sci. 20 (1998) 359–361). One somaclone was selected with robust plant type and vigorous growth yielding essential oil in the range of 0.4 to 0.6% and showing enhanced bioactivity. The essential oil of this somaclone was very effective (almost four fold more) against stored grain pest *Tribolium castaneum* as herbal fumigant. In addition it showed substantial activity against other stored grain pests like *Callosobruchus maculates* (pulse beetle), *Rhyzopertha dominica* (lesser grain borer), *Sitophilus oryzae* (rice weevil). Further testing for the anti-microbial activities the oil showed substantially higher antibacterial and antifungal properties. In addition it also had a remarkable potato sprouting inhibition activity. This plant being edible is safe for all food application thus the novel plant of this invention was developed which yields a rare essential oil with multipurpose use.

Upon obtaining a plant with essential oil having desirable antimicrobial and anti-insect properties the applicants followed a procedure for inducing in vitro variability to select high yielding genotype(s) in form of somaclonal variants. The applicants generated 188 independent calliclones as plantlets from this accession of *Mentha spicata* L. var. *viridis*. These clones were subjected to detection of molecular variation at the tissue culture stage itself through RAPD profiling. DNA was isolated from 40 mg of leaf tissue and Polymerase chain reactions (PCRs) were carried out in 25 μl volume. A reaction tube contained 25 ng of DNA, 0.2 unit of Taq DNA polymerase, 100 μl each of dNTPs, 1.5 mM $MgCl_2$ and 5 p mol of decanucleotide primers. The amplifications were carried out using a thermal cycler (MJ Research, USA). The amplified products were loaded in 1.2% agarose gel containing 0.5 μg $ml^{-1}$ of ethidium bromide and photographed by Polaroid system. Twelve decamer primers having the sequences AAATCGGAGC, GTCCTACTCG, GTCCTTAGCG, TGCGCGATCG, AACGTACGCG, GCACGCCGGA, CACCCTGCGC, CTATCGCCGC, CGGGATCCGC, GCGAATTCCG, CCCTGCAGGC, CCAAGCTTGC were synthesized and used to analyze all the in vitro regenerated clones. Out of 188 regenerated clones 9 showed distinct variation at DNA level in the RAPD profiles compared to the control plant (parent accession).

These 9 clones were hardened and transferred to glasshouse in pots and subsequently to the field. Among these clones, one clone G-3-97 (hereafter referred as 'Ganga') showed conspicuously uniform and vigorous growth characteristics and attained much higher height and shoot proliferation. Its essential oil yield was in the range of 0.4–0.6% compared to 0.1–0.2% of the parental genotype. Further the plant was uniformly green throughout the year when subjected to intermittent cutting schedules of 30 to 90 days. Randomly 100 regenerated shoots from the clone were tested for variation in their profiles using the above-described 12 random primers. Complete uniformity was observed among these clones all being clearly distinct from the initial parent accession from the bank of the river Ganga. Considering the distinctiveness, the plant developed was stabilized in the field and accessioned in the "National Gene Bank" and maintained in the field.

Bioactivity

Upon evaluating bioactivity of the essential oils of all the accessions of *Mentha spicata* L var. *viridis* including parent plant against *Tribolium castaneum*(flour beetle), *Callosobruchus maculates* (pulse beetle), *Rhyzopertha dominica* (lesser grain borer), *Sitophilus oryzae* (rice weevil), the oil from the plant Ganga was found to be most effective. In these experiments, the most problematic stored grain insect pest *Tribolium castaneum* (flour beetle), *Callosobruchus maculates* (pulse beetle), *Rhyzopertha dominica* (lesser grain borer), *Sitophilus oryzae* (rice weevil) were used as target pests. Varying dosages levels (1 μl, 5 μl, 10 μl 20 μl and 40 μl/L of air space in containers used for grain storage) were tested with 15 replications per dose and 20 adult insects per replication. The mortality percentage was recorded after 24 hours. The major constituents of the essential oil of the plant 'Ganga' had limolene (1.38%) and piperitenone oxide (73.13%)

Potential of 'Ganga' essential oil as herbal fumigant agent against stored grain pest

| | % mortality of insects (adults) after 24 hours | | | |
|---|---|---|---|---|
| Amount of oil Per liter air volume (μl) | Pulse beetle (1) | Lesser Rice grain borer (2) | Rice weevil (3) | Flour beetle (4)* |
| 0 | 0 | 0 | 0 | 0 |
| 1 | 20 | 0 | 0 | 0 |
| 3 | 30 | 10 | 5 | 0 |
| 5 | 70 | 30 | 30 | 20 |
| 7 | 100 | 100 | 100 | 50 |
| 10 | 100 | 100 | 100 | 100 |

*1. *Callosobruchus maculates,*
2. *Rhyzopertha dominica,*
3. *Sitophillus oryzae,*
4. *Tribolium castaneum*

It was evident from the mortality data in the bioassays that the essential oil of the new plant developed (Ganga) was highly potent as herbal fumigant against stored grain pests *Tribolium castaneum* (flour beetle), *Callosobruchus maculates* (pulse beetle), *Rhyzopertha dominica* (lesser grain borer), *Sitophilus oryzae* (rice weevil) for which hardly any biopesticide is available. Thus the oil of the plant 'Ganga' can be used as a herbal fumigant at a concentration as low as 10 μl in a space of 1 liter containing stored food which is very effective at lower doses ($10^{-5}$ volume required).

Since parent plant oil had shown antibacterial activity against *Escherichia coli, Klebsiella pneumoniae, Streptococcus mutans, Staphylococcus epidermidis, Enterobacter aerogenes, Enterococcus feacalis, Staphylococcus aureus* and antifungal activity against *Aspergillus flavus, Aspergillus niger, Candida albicans, Microsporum gypseum, Sporothrix schenckii* strains, the Applicants evaluated oil of 'Ganga' also for its activity. As evident in table below, the oil exhibited substantial antimicrobial activity and in different dilutions was found to control broad spectrum bacteria including *Escherichia coil, Klebsiella pneumoniae, Streptococcus mutans, Staphylococcus epidermidis, Enterobacter aerogenes, Enterococcus feacalis, Staphylococcus aureus* and antifungal activity against *Aspergillus flavus, Aspergillus niger, Candida albicans, Microsporum gypseum, Sporothrix schenckii.*

1. Considering the involvement of *Streptococcus mutans* in buccal cavity for bad breath the oil can be used for mouth wash.
2. As the oil is effective against *Aspergillus* which are responsible of spoilage of raw, processed and cooked food commodities, can be used as a bio-preservant.
3. As the oil is effective against dermatophytic microbes like *Candida albicans, Microsporum gypseum* and *Staphylococcus epidermidis* can be used for shampoo and soap.
4. Considering the broad spectrum anti-bacterial and anti-fungal activity of the oil, this can be used as surface and hand disinfectant.

Minimum inhibitory concentrations of the essential oil at which the growth of the microorganism is checked.

| Fungal strains | Concentration of essential oil of 'Ganga' at which the growth is inhibited | Concentration of essential oil of 'Supriya' at which the growth is inhibited |
|---|---|---|
| *Aspergillus flavus* | 1/400 | 1/200 |
| *Aspergillus niger* | 1/800 | 1/400 |
| *Candida albicans* | 1/400 | 1/200 |
| *Microsporum gypseum* | 1/6400 | 1/800 |
| *Sporothrix schenckii* | 1/400 | 1/200 |
| *Trichophyton rubrum* | 1/800 | 1/400 |

| Bacterial strains | Concentration of essential oil of 'Ganga' at which the growth is inhibited |
|---|---|
| *Escherichia coli* | 1/400 |
| *Klebsiella pneumoniae* | 1/400 |
| *Streptococcus mutans* | 1/1600 |
| *Staphylococcus epidermidis* | 1/800 |
| *Enterobacter aerogenes* | 1/400 |
| *Enterococcus feacalis* | 1/800 |

Experiments were conducted for the activity of the oil obtained from 'Ganga' to suppress potato sprouting. It was found that in a closed container of 1-lit volume a minimum of 10 μl of oil the sprouting of potato can be restricted and also preserve these from microbial attack.

The above experiments established the scope of multipurpose use of the novel plant 'Ganga' where oil from 45–60 days old leaves can be used as herbal fumigant for storage of grains, flour and other food materials. Traditionally the plant var. *viridis* leaves are consumed by humans as food adjuvant for different purposes and hence is non toxic, environmentally safe, pleasant in aroma and hence best source for herbal insect control agent for stored grain insects which carries enormous economic potential in terms of preventing post harvest losses.

Emphasis in development of this better plant type was laid on herbage yield and higher essential oil productivity. The plant of invention was tested in field trial for oil yield, presence of oil constituents in different seasons and herbage production against the existing & common variety cv. Supriya (released variety for carvone rich oil). Replicated field trials were conducted following normal agronomic practices by planting multiplied suckers in the month of January, 1998 and 1999 for 2 consecutive years in RBD fashion and different growth and yield characteristics were recorded (Table 1) by harvesting the plant at one month intervals. The control plant 'Supriya' started showing senescence and dried up in the month of August. For field trials 10 m×10 m plots were prepared by adding only FYM @1.5 ton per ha. The plant 'Ganga' completely out-competed the existing variety for its rate of growth and essential oil production.

TABLE 1

Comparative growth and yield characteristics of plant of invention 'Ganga' in relation to the existing variety 'Supriya'

| Property | Ganga | Supriya |
|---|---|---|
| Plant height (cm) | 68–77 | 37–50 |
| Branch length (cm) | 42–57 | 19–30 |
| Leaves per branch | 22–32 | 14–20 |
| Leaf length | 4.9–5.7 | 2.9–4.0 |
| Leaf breadth | 2.6–3.0 | 1.8–2.3 |
| Petiole length | 0.4–0.7 | 0.3–0.5 |
| Oil % | 0.36 to 0.65 | 0.20 to 0.46 |
| Leaf to stem ratio | 1.387 | 1.281 |
| Leaf area ($cm^2$) | 8.41 | 2.26 |
| Weight of aerial part of single plant (g) | 278.38 | 61.29 |
| Weight of suckers produced per plant (g) | 341.75 | 42.167 |
| Ratio of suckers to aerial plant part | 1.228 | 0.688 |
| Herbage yield in kg/100 $m^2$ | 165.2 | 120.0 |

Taxonomic description of the mint plant 'Ganga'

1. *Genus.—Mentha.*
2. *Species.—spicata* L. var. *viridis.*
3. *Family.*—Lamiaceae.
4. *Common name.*—Spear mint.
5. *Plant height.*—68–77 cm.
7. *Growth habit.*—Erect sturdy main stem, profuse synchronous branching, profuse runners with growth habit giving globular shape to the canopy (FIG. 1*a*).
8. *Stem.*—Round to quadrangular hard, woody, with hairy surface texture, faint purplish red (59A) pigmentation, 5–10 mm thick at $5^{th}$ internode, number of nodes in the main branch 15 to 25.
9. *Leaf.*—Colour: Upper surface light green (137B to 137C), lower surface light green (147B). Texture: Moderately thick and rigid. Surface: Rough with depressed veins and vein lets. Shape: Ovate to Lacerate. Margin: Moderately deep serration (18 to 40 number). Tip: Acute. Size: Leaf length 4.5 to 7.0 cm, breadth 2.0 to 4.5 cm when full grown. Petiole length: 0.5 to 0.7 cm, colour faint purplish (59C).

*10. Leaf.*—Stem ratio (w/w): 1.387.

*11. Inflorescence.*—Indefinite recemose. Flower shape: Tubular. Flower diameter: About 2 mm. Pedicel length: 0.5 to 1.5 mm. Pedicel colour: Yellow green (146C). Calyx: 4 sepals, gamosepalous, 1 mm diameter. Calyx colour: Yellow green (146C). Corolla: 4 petals, gamopetalous, tubular, average diameter 3–4 mm, smooth surface texture. Corolla colour: Purple (76D). Anthers: 4, didynamous, red purple (59A), 0.2 mm to 0.4 mm. Stigma: Bifid, red purple (59A). Ovary: Bicarpellary, Syncarpous, Yellow green (151A).

*Fruit/seed.*—None observed.

*Flower fragrance.*—None observed.

*Leaf fragrance.*—Bitter minty carvone.

The colour codes are in accordance with The R.H.S. colour chart published by The Royal Horticultural Society, 80 Vincent Square, London SW1P 2PE, 1995.

| | Oil composition | | |
|---|---|---|---|
| Plant | Limonene (%) | Carvone (%) | Piperitenone oxide (%) |
| Ganga | 1.50 to 6.52 | 0.10 to 4.42 | 28.50 to 77.48 |
| Supriya | 1.15 to 26.78 | 58.79 to 65.39 | Trace to 0.395 |

As described above there is a significant difference of the oil yield and composition, which varies at different stages of growth. The essential oil of plant 'Ganga' accumulates more of the constituent piperitenone oxide at any time of the year compared to the existing variety 'Supriya' and this oil composition gives typically high activity for controlling stored grain pest. Thus the oil composition of this kind even if chemically resynthesises, can be used for similar purpose. The plant can be harvested at any point of time during the year and young leaves can be used as adjuvant to different food and beverages. Another utility of the plant is, if the piperitenone oxide is solicited then the plants should be harvested with leaves of 45 days or more growth during March to November. After first cut in March for January planted crop, at least six additional harvests can be made for shoots to distill oil of above said activities.

Essential oil composition (average) of the plant 'Ganga' at different time of the year when planted in the 4th week of January.

| Time of the year | Limonene (%) | Carvone (%) | Piperitenone oxide (%) |
|---|---|---|---|
| January–February | 1.50 | 4.42 | 36.70 |
| March–April | 5.68 | 0.20 | 72.30 |
| May–June | 2.08 | 0.25 | 80.45 |
| July–August | 4.75 | 0.10 | 77.48 |
| September–October | 6.52 | 0.12 | 71.83 |
| November | 3.92 | 0.18 | 64.59 |
| December | 2.74 | 0.13 | 28.50 |

The plant 'Ganga' compared to other culinary variety 'Supriya' and other varieties possesses a distinct aroma due to the difference in chemical constituents. The tender plants coming out within one month of harvest are suitable for consumption, where as more than two month old plants contained varied amount of essential oil components as described above and can be harvested according to the requirements.

Culinary and dried herb value of 'Ganga' were assessed by using the leaves (fresh and dried) for tea blending and chutney (ketchup) as follows. The young leaves from plants were plucked after 20 to 30 days after the harvest for oil extraction and dried to a moisture percentage of 6 to 10% at 37° C. temperature. The leaves were then hand crushed to flakes and mixed with commercial tea grains (10 to 30%). Tea bags with normal tea without the mint leaf and with mint leaves were offered to 20 human volunteers for tea testing over 10 alternate days. Among them 16 (80%) of the volunteers after taking both the tea types showed the desire for mint tea containing 15 to 20% leaves of the plant 'Ganga'. The dried and fresh herb was also offered to 10 volunteers for trying in chutney or ketchup from young plants of one month after first cutting and more than 2 month old plants after cutting. Seven volunteers preferred for one month young plants and no one preferred older leaves.

Evidence of Uniformity and Stability

No variants of any kind (morphological or molecular) have been observed since 1997 indicating the stability and uniformity of the genotype. It is clear from these results that the 'Ganga' cultivar is stable and reproduces true to type in successive generations of asexual reproduction. Further, the comparative per plant herb and oil yields of 'Ganga' were significantly higher in comparison to available varieties over years and seasons. Due to vigorous vegetative growth this genotype can be harvested at any time of the year and has the potential of growing on slopes of water channels.

Statement of Distinction

The genotype 'Ganga' is unique which grows vigorously and can be maintained green throughout the year with proper harvesting scheduling where as the existing varieties do not possess these characters. Further, the plant 'Ganga' can be variously harvested for oil constituents and herb material for different utilities by scheduling harvesting at different period of the year. The genotype produces better biomass (leaf and sucker) and oil in comparison to others. Its genetic make up is distinct in terms of DNA profile.

The 'Ganga' cultivar is distinguished from its parent, inter alia, by its distinct DNA pattern detailed below, a higher yield of essential oil (0.4–0.6% compared with 0.1–0.2% in the parent).

Randomly Amplified Polymorphic DNA Analysis

The RAPD profiles of the plant 'Ganga' were unambiguously able to establish its distinct identity as completely different from the parent plant as well as the known released variety "Supriya" (FIG. 1*d*). Screening molecular variants (somaclones) from cloned population had already differentiated as distinct, unique and novel at DNA level. The plant of the present invention being one of these variants had a unique RAPD profile (FIG. 1*c*). The plant is having desirable morphological and economical traits in a rare unmatchable combination and is available only at CIMAP. No variation in the RAPD patterns was observed in the analysis of the micropropagated as well as field raised population in successive generations indicating the stability of the genotype. The following random primers synthesized in the laboratory with the sequence AAATCGGAGC (SEQ ID NO: 1), GTCCTACTCG (SEQ ID NO: 2), GTCCTTAGCG (SEQ ID NO: 3), TGCGCGATCG (SEQ ID NO: 4), AACGTACGCG (SEQ ID NO: 5), GCACGCCGGA (SEQ ID NO: 6), CTATCGCCGC (SEQ ID NO: 7), CGGGATCCGC (SEQ ID NO: 8), GCGAATTCCG (SEQ ID NO: 9), CCCTGCAGGC (SEQ ID NO: 10), CCAAGCTTGC (SEQ ID NO: 11), GTGCAATGAG (SEQ ID NO: 12), AGGATACGTG (SEQ ID NO: 13), AAGATAGCGG (SEQ ID NO: 14), GGATCTGAAC (SEQ ID NO: 15), TTGTCTCAGG (SEQ ID NO: 16), CATCCCGAAC (SEQ ID NO: 17), GGACTCCACG (SEQ ID NO: 18) were used for the analysis of distinctiveness.

The plant of invention can be easily grown on slopes of water channels as given in FIG. 1*b* and plot bunds without affecting area winter main crop. It is possible to take upto 8 harvests of same oil quality from January through December.

The essential oil of the plant has multiple uses which includes most importantly the agroprotectant of agriculture produce and stored grains in household levels to warehouses. Antimicrobial properties of the essential oil make the oil useful as biopreservate and in antimicrobial formulations of diverse kinds. The plant as such, being edible, is non-toxic and safe to humans, animals, plants and environment.

SEQUENCE LISTING

```
<160> NUMBER OF SEQ ID NOS: 18

<210> SEQ ID NO 1
<211> LENGTH: 10
<212> TYPE: DNA
<213> ORGANISM: Artificial Sequence
<220> FEATURE:
<223> OTHER INFORMATION: Description of Artificial Sequence: Primers
      used for RAPD analysis of plant 'Ganga' to establish its distinct
      identity

<400> SEQUENCE: 1

aaatcggagc                                                          10


<210> SEQ ID NO 2
<211> LENGTH: 10
<212> TYPE: DNA
<213> ORGANISM: Artificial Sequence
<220> FEATURE:
<223> OTHER INFORMATION: Description of Artificial Sequence: Primers
      used for RAPD analysis of plant 'Ganga' to establish its distinct
      identity

<400> SEQUENCE: 2

gtcctactcg                                                          10


<210> SEQ ID NO 3
<211> LENGTH: 10
<212> TYPE: DNA
<213> ORGANISM: Artificial Sequence
<220> FEATURE:
<223> OTHER INFORMATION: Description of Artificial Sequence: Primers
      used for RAPD analysis of plant 'Ganga' to establish its distinct
      identity

<400> SEQUENCE: 3

gtccttagcg                                                          10


<210> SEQ ID NO 4
<211> LENGTH: 10
<212> TYPE: DNA
<213> ORGANISM: Artificial Sequence
<220> FEATURE:
<223> OTHER INFORMATION: Description of Artificial Sequence: Primers
      used for RAPD analysis of plant 'Ganga' to establish its distinct
      identity

<400> SEQUENCE: 4

tgcgcgatcg                                                          10


<210> SEQ ID NO 5
<211> LENGTH: 10
<212> TYPE: DNA
```

-continued

<213> ORGANISM: Artificial Sequence
<220> FEATURE:
<223> OTHER INFORMATION: Description of Artificial Sequence: Primers used for RAPD analysis of plant 'Ganga' to establish its distinct identity

<400> SEQUENCE: 5 aacgtacgcg 10

<210> SEQ ID NO 6
<211> LENGTH: 10
<212> TYPE: DNA
<213> ORGANISM: Artificial Sequence
<220> FEATURE:
<223> OTHER INFORMATION: Description of Artificial Sequence: Primers used for RAPD analysis of plant 'Ganga' to establish its distinct identity

<400> SEQUENCE: 6 gcacgccgga 10

<210> SEQ ID NO 7
<211> LENGTH: 10
<212> TYPE: DNA
<213> ORGANISM: Artificial Sequence
<220> FEATURE:
<223> OTHER INFORMATION: Description of Artificial Sequence: Primers used for RAPD analysis of plant 'Ganga' to establish its distinct identity

<400> SEQUENCE: 7 ctatcgccgc 10

<210> SEQ ID NO 8
<211> LENGTH: 10
<212> TYPE: DNA
<213> ORGANISM: Artificial Sequence
<220> FEATURE:
<223> OTHER INFORMATION: Description of Artificial Sequence: Primers used for RAPD analysis of plant 'Ganga' to establish its distinct identity

<400> SEQUENCE: 8 cgggatccgc 10

<210> SEQ ID NO 9
<211> LENGTH: 10
<212> TYPE: DNA
<213> ORGANISM: Artificial Sequence
<220> FEATURE:
<223> OTHER INFORMATION: Description of Artificial Sequence: Primers used for RAPD analysis of plant 'Ganga' to establish its distinct identity

<400> SEQUENCE: 9 gcgaattccg 10

<210> SEQ ID NO 10
<211> LENGTH: 10
<212> TYPE: DNA
<213> ORGANISM: Artificial Sequence
<220> FEATURE:
<223> OTHER INFORMATION: Description of Artificial Sequence: Primers used for RAPD analysis of plant 'Ganga' to establish its distinct identity

<400> SEQUENCE: 10

-continued ccctgcaggc 10

<210> SEQ ID NO 11
<211> LENGTH: 10
<212> TYPE: DNA
<213> ORGANISM: Artificial Sequence
<220> FEATURE:
<223> OTHER INFORMATION: Description of Artificial Sequence: Primers used for RAPD analysis of plant 'Ganga' to establish its distinct identity

<400> SEQUENCE: 11 ccaagcttgc 10

<210> SEQ ID NO 12
<211> LENGTH: 10
<212> TYPE: DNA
<213> ORGANISM: Artificial Sequence
<220> FEATURE:
<223> OTHER INFORMATION: Description of Artificial Sequence: Primers used for RAPD analysis of plant 'Ganga' to establish its distinct identity

<400> SEQUENCE: 12 gtgcaatgag 10

<210> SEQ ID NO 13
<211> LENGTH: 10
<212> TYPE: DNA
<213> ORGANISM: Artificial Sequence
<220> FEATURE:
<223> OTHER INFORMATION: Description of Artificial Sequence: Primers used for RAPD analysis of plant 'Ganga' to establish its distinct identity

<400> SEQUENCE: 13 aggatacgtg 10

<210> SEQ ID NO 14
<211> LENGTH: 10
<212> TYPE: DNA
<213> ORGANISM: Artificial Sequence
<220> FEATURE:
<223> OTHER INFORMATION: Description of Artificial Sequence: Primers used for RAPD analysis of plant 'Ganga' to establish its distinct identity

<400> SEQUENCE: 14 aagatagcgg 10

<210> SEQ ID NO 15
<211> LENGTH: 10
<212> TYPE: DNA
<213> ORGANISM: Artificial Sequence
<220> FEATURE:
<223> OTHER INFORMATION: Description of Artificial Sequence: Primers used for RAPD analysis of plant 'Ganga' to establish its distinct identity

<400> SEQUENCE: 15 ggatctgaac 10

<210> SEQ ID NO 16
<211> LENGTH: 10
<212> TYPE: DNA
<213> ORGANISM: Artificial Sequence
<220> FEATURE:

-continued

```
<223> OTHER INFORMATION: Description of Artificial Sequence: Primers
      used for RAPD analysis of plant 'Ganga' to establish its distinct
      identity

<400> SEQUENCE: 16

ttgtctcagg                                                          10


<210> SEQ ID NO 17
<211> LENGTH: 10
<212> TYPE: DNA
<213> ORGANISM: Artificial Sequence
<220> FEATURE:
<223> OTHER INFORMATION: Description of Artificial Sequence: Primers
      used for RAPD analysis of plant 'Ganga' to establish its distinct
      identity

<400> SEQUENCE: 17

catcccgaac                                                          10


<210> SEQ ID NO 18
<211> LENGTH: 10
<212> TYPE: DNA
<213> ORGANISM: Artificial Sequence
<220> FEATURE:
<223> OTHER INFORMATION: Description of Artificial Sequence: Primers
      used for RAPD analysis of plant 'Ganga' to establish its distinct
      identity

<400> SEQUENCE: 18

ggactccacg                                                          10
```

We claim:

1. A novel and distinct variety of *Mentha spicata* L. var. *viridis* plant, as illustrated and described herein

* * * * *